United States Patent [19]
Fukumoto et al.

[11] Patent Number: 6,060,609
[45] Date of Patent: May 9, 2000

[54] PROCESS FOR PRODUCING AND METHOD OF CRYSTALLIZING 2-AZABICYCLO[2.2.1] HEPT-5-EN-3-ONE

[75] Inventors: Takashi Fukumoto; Rensuke Ikarashi, both of Kitakanbara-gun, Japan

[73] Assignee: Kuraray Co., Ltd., Kurashiki, Japan

[21] Appl. No.: 09/220,750

[22] Filed: Dec. 28, 1998

[30] Foreign Application Priority Data

Dec. 25, 1997 [JP] Japan .................................. 9-366169
Dec. 25, 1997 [JP] Japan .................................. 9-366170

[51] Int. Cl.[7] ................................................. C07D 209/52
[52] U.S. Cl. ............................................................. 548/512
[58] Field of Search .............................................. 548/512

[56] References Cited

U.S. PATENT DOCUMENTS

| | | | |
|---|---|---|---|
| 5,200,527 | 4/1993 | Griffiths et al. | 548/452 |
| 5,300,649 | 4/1994 | Griffiths et al. | 546/290 |
| 5,847,157 | 12/1998 | Romanowski et al. | 548/512 |

FOREIGN PATENT DOCUMENTS

| | | |
|---|---|---|
| 0 533 048 | 3/1993 | European Pat. Off. . |
| 5-331139 | 12/1993 | Japan . |
| 5-331140 | 12/1993 | Japan . |
| 8-27110 | 1/1996 | Japan . |
| 9-165372 | 6/1997 | Japan . |
| WO 96-06080 | 2/1996 | WIPO . |

OTHER PUBLICATIONS

Chemical Abstracts, AN 316997, vol. 124, No. 23, Jun. 3, 1996, JP 8–027110, Jan. 30, 1996.

Chemical Abstracts, AN108526, vol. 121, No. 09, Aug. 29, 1994, JP 05 331140, Dec. 14, 1993.

J. Org. Chem., 1985, vol. 50, 1983–1985, An Approach to the Synthesis of Neplanocin A, William C. Faith et al.

J. Org. Chem., 1993, vol. 58, 6129–6131, Diels–Alder Reaction of Methanesulfonyl Cyanide with Cyclopentadiene. Industrial Synthesis of 2–Azabicyclo[2.2.1] Hept–5–En–3–One, Gareth J. Griffiths, et al.

Chem. Pharm. Bull., vol. 44, 1996, 850–852, Hetero Diels–Alder Reaction of Benzenesulfonyl Cyanide With Cyclopentadiene Using Chiral Lewis Acids, Nobuya Katagiri et al.

J. Org. Chem., vol. 39, No. 4, 1974, 564–566, Diels–Alder Cycloadditions of Sulfonyl Cyanides with Cyclopentadiene. Synthesis of 2–Azabicyclo[2.2.1]Hepta–2,5–Dienes, J. C. Jagt et al.

J. Org. Chem., vol. 43, No. 12, 1978, 2311–2320, Synthesis of Carbocyclic Aminonucleosides, Susan Daluge et al.

J. Org. Chem., vol. 46, 1981, 3268–3272, Carbocyclic Sugar Amines: Synthesis and Stereochemistry of Racemic α– and B–Carbocyclic Ribofuranosylamine, Carbocyclic Lysofuranosylamine, and Related Compounds, Bernard L. Kam, et al.

J.C.S. Perkin I, 874–884, Reaction of Chlorosulphonyl Isocyanate With 1,3–Dienes. Control of 1,2– and 1,4–Addition Pathways and the Synthesis of Aza– and Oxa–Bicyclic Systems, J.R. Malpass, et al., Jul. 1976.

*Primary Examiner*—Joseph McKane
*Attorney, Agent, or Firm*—Oblon, Spivak, McClelland, Maier & Neustadt, P.C.

[57] ABSTRACT

A process for producing 2-azabicyclo[2.2.1]hept-5-en-3-one is provided by reacting a sulfonyl cyanide represented by the general formula R-SO$_2$CN (in which R represents an alkyl group or a phenyl group which may have a substituent), in the presence of water and in a hydrocarbon solvent at a pH of 4 to 7 inclusive. 2-Azabicyclo[2.2.1]hept-5-en-3-one can be produced in a high yield and a high purity in one step process, with a reduced amount of solvent used, safely and with good productivity. A method of crystallizing 2-azabicyclo[2.2.1]hept-5-en-3-one is also provided, which includes dissolving 2-azabicyclo[2.2.1]hept-5-en-3-one into an organic solvent mainly including at least one of diisopropyl ether and methyl tertiary butyl ether, cooling the solution to deposit crystals of 2-azabicyclo[2.2.1]hept-5-en-3-one. Finely divided particulate crystals of 2-azabicyclo[2.2.1]hept-5-en-3-one excellent in fluidity and handleability can be obtained with a simple procedure and in a high recovery rate.

13 Claims, No Drawings

PROCESS FOR PRODUCING AND METHOD OF CRYSTALLIZING 2-AZABICYCLO[2.2.1]HEPT-5-EN-3-ONE

BACKGROUND OF THE INVENTION

FIELD OF THE INVENTION

The present invention relates to a process for producing 2-azabicyclo[2.2.1]hept-5-en-3-one and a method of crystallizing 2-azabicyclo[2.2.1]hept-5-en-3-one into finely divided particulate crystals.

DISCUSSION OF THE BACKGROUND

Carbocyclic nucleosides have a structure in which an oxygen atom of the furanose ring of the nucleoside is substituted with a methylene group; the structure is similar to a nucleoside having a furanose ring, and it can act as a substrate or an inhibitor for various enzymes in living bodies. Since the carbocyclic nucleosides do not have a glycoside bonding, they are not subject to cleaving or splitting by enzymes such as nucleoside phospholylase or nucleoside hydrase, they have a different metabolic pathway from nucleosides having the furanose ring, and they exhibit various physiological activities.

For example, carbocyclic adenosine, also known as Aristeromycin, is a type of carbocyclic nucleoside that is a metabolite of Streptomyces citricolor and has been noted for its strong cytotoxicity, in contrast to nucleosides having the furanose ring.

Carbocyclic-2,3-dideoxy-2,3-didehydroguanosine, a type of carbocyclic nucleoside, has now been developed as an anti-HIV agent [R. Vince, et al., Biochem. Biophys. Res. Commun. 156, 1046 (1988)].

The carbocyclic part of the carbocyclic nucleoside is often formed by using, for example, $2\alpha$, $3\alpha$-dihydroxy-$4\beta$-aminocyclopentanone-$1\beta$-methanol or cis-4-aminocyclopent-2-en-$1\beta$-methanol. Such $1\beta$-methanols are often chemically synthesized from 2-azabicyclo[2.2.1]hept-5-en-3-one [R. Vince, et al., J. Org. Chem., 43, 2311 (1978); B. L. Kamm, et al., J. Org. Chem., 46, 3268 (1981); W. C. Faith, et al., J. Org. Chem., 50, 1983 (1985)]. Accordingly, 2-azabicyclo[2.2.1]hept-5-en-3-one is useful as an intermediate for synthesizing $1\beta$-methanols and, thus, carbocyclic nucleosides.

As a method for synthesizing 2-azabicyclo[2.2.1]hept-5-en-3-one, a process of subjecting cyclopentadiene and p-toluenesulfonyl cyanide to a cyclizing addition reaction to form 3-p-toluenesulfonyl-2-azabicyclo[2.2.1]hepta-2,5-diene as an intermediate product and removing the toluenesulfonyl group on the 3-position in the intermediate product by using acetic acid is known [J. C. Jagt. et al., J. Org. Chem., 39, 564 (1974); R. Vince, et al., J. Org. Chem., 43, 2311 (1978)].

However, the synthesizing process described above involves various problems, for example, in that (1) cyclopentadiene, which may be used theoretically in an equimolar amount to p-toluenesulfonyl cyanide, must actually be used in a great excess of 15 to 35 molar times inclusive; (2) it is laborious and time consuming since the process is a multi-step reaction; (3) 3-p-toluenesulfonyl-2-azabicyclo[2.2.1]hepta-2,5-diene obtained by the reaction of p-toluenesulfonyl cyanide and cyclopentadiene has to be condensed and taken out as lumps, which are pulverized into powder and then reacted with acetic acid; (4) acetic acid has to be added in a great excess of 5 to 23 molar times inclusive all at once upon removing the toluenesulfonyl group at the 3-position by treating 3-p-toluenesulfonyl-2-azabicyclo[2.2.1]hepta-2,5-diene with acetic acid, so that abrupt exothermic reaction must be controlled; (5) if the exothermic reaction in (4) cannot be satisfactorily controlled and the reaction temperature rises excessively, the product, 2-azabicyclo[2.2.1]hept-5-en-3-one, cannot be obtained at all or is obtainable only at an extremely low yield; (6) solid by-products are formed upon reaction in (4) which hinder smooth stirring and the reaction cannot proceed smoothly; and (7) a great amount of waste water is formed, which increases the burden for treating the same. Therefore, by the synthesis process described above, 2-azabicyclo[2.2.1]hept-5-en-3-one cannot be produced industrially in a high purity and a high yield with a reduced amount of reagent and solvent, safely and with good productivity.

Under the circumstances as described above, the present inventors have continued studies for developing a process capable of producing 2-azabicyclo[2.2.1]hept-5-en-3-one in a high purity and a high yield with a reduced amount of reagent and solvent, safely and with good productivity. Then, we have found the following processes and filed them already: (i) a process for producing 2-azabicyclo[2.2.1]hept-5-en-3-one by way of a first step of condensing sulfonyl cyanide and cyclopentadiene in a hydrocarbon solvent and then a second step of treating with water (Japanese Published Unexamined Patent Application Hei 5-331139), (ii) a process for producing 2-azabicyclo[2.2.1]hept-5-en-3-one by reacting sulfonyl cyanide and cyclopentadiene in water or a mixed solvent of water and a hydrocarbon (Japanese Published Unexamined Patent Application Hei 5-331140); (iii) a process for producing 2-azabicyclo[2.2.1]hept-5-en-3-one by reacting benzenesulfonyl cyanide and cyclopentadiene in a mixed solvent of water and a water soluble solvent under a pH condition of from 3 to 4 inclusive (Japanese Published Unexamined Patent Application Hei 8-27110); and (iv) a process for producing 2-azabicyclo[2.2.1]hept-5-en-3-one by reacting sulfonyl cyanide and cyclopentadiene in a hydrocarbon solvent to form 3-sulfonyl-2-azabicyclo[2.2.1]hepta-2,5-diene as an intermediate product and hydrolyzing the intermediate product by adding a solution of the intermediate product into a mixed solvent of water and a water soluble solvent under a pH condition of from 3 to 7 inclusive (Japanese Published Unexamined Patent Application Hei 9-165372).

When compared with the existing process by J. C. Jagt, et al., i.e., a process for producing 2-azabicyclo[2.2.1]hept-5-en-3-one by reacting acetic acid with 3-p-toluenesulfonyl-2-azabicyclo[2.2.1]hepta-2,4-diene prepared by the reaction of cyclopentadiene and p-toluenesulfonyl cyanide, the production processes (i)–(iv) described above have various advantages such that:

(1) it is not necessary to use cyclopentadiene in a great excess relative to sulfonyl cyanide;

(2) no troublesome procedures are required for taking out 3-p-toluenesulfonyl-2-azabicyclo[2.2.1]hepta-2,5-diene as the intermediate product in a condensed form, pulverizing the same into powder, then subjecting to the succeeding step;

(3) since no abrupt exothermic reaction takes place, reaction control is easy and the reaction is safe;

(4) the yield of the 2-azabicyclo[2.2.1]hept-5-en-3-one is high;

(5) solid by-products which hinder the stirring during the reaction are reduced; and (6) the amount of waste water to be treated is small, which moderates the processing burden.

Each of the processes (i) and (iv) above is conducted by way of two steps: reacting sulfonyl cyanide and cyclopentadiene in a hydrocarbon solvent in the first step to form 3-sulfonyl-2-azabicyclo[2.2.1]hepta-2,5-diene as an intermediate product; and then processing the solution of the intermediate product in water or a mixed solvent of water and a water soluble solvent in the second step to produce 2-azabicyclo[2.2.1]hept-5-en-3-one.

On the other hand, each of the processes (ii) and (iii) above is a process for directly producing 2-azabicyclo[2.2.1] hept-5-en-3-one by reacting sulfonyl cyanide and cyclopentadiene in water or a mixed solvent of water and a hydrocarbon solvent or in a mixed solvent of water and a water soluble solvent in one step. This process is more simple than the two step processes (i) or (iv) above and is industrially advantageous.

However, in method (ii), the pH is not controlled during the reaction of sulfonyl cyanide and cyclopentadiene, and it has been found that the pH in the reaction mixture is 3 or lower (generally pH 2 to 3 inclusive) due to sulfonyl cyanide present in the mixture or sulfinic acid (for example, benzenesulfinic acid) formed by reaction. In this case, it is difficult to completely prevent deposition, in the reaction mixture, of solid products such as dimerization products (for example, benzenesulfinyl sulfone) of sulfinic acid resulted from the reaction of sulfonyl cyanide and cyclopentadiene (for example, benzenesulfinic acid), and this requires a filtration step for the deposited solid products. Then, if deposition of the solid products is to be completely prevented, a great amount of water or hydrocarbon solvent has to be used, which increases the burden on the waste water treatment and leaves room for improvement.

In method (iii) above, sulfonyl cyanide and cyclopentadiene are reacted under a pH condition of from 3 to 4 inclusive and it is difficult to completely prevent deposition of dimerization products (for example, benzenesulfinyl sulfone) of sulfinic acid (for example, benzenesulfinic acid) perhaps because a mixed solvent of water and a water soluble solvent is used as a solvent. Further, method (iii) gives a lower yield for 2-azabicyclo[2.2.1]hept-5-en-3-one, compared with the process (ii) described above.

SUMMARY OF THE INVENTION

One object of the present invention is to provide an improved process capable of producing 2-azabicyclo[2.2.1] hept-5-en-3-one in high purity on industrial scale.

Another object of the present invention is to provide a process in which the deposition of dimerization products (for example, benzenesulfinyl sulfone) of sulfinic acid (for example, benzenesulfinic acid) can be completely prevented, inhibition of stirring is eliminated, a filtration step for the solution after completion of the reaction is eliminated, and the 2-azabicyclo[2.2.1]hept-5-en-3-one can be produced in a high purity and a high yield, safely and with a good productivity.

Another object of the present invention is to provide a process in which the reaction can be conducted with no deposition of solid products even if the amount of water or the hydrocarbon solvent to be used is reduced.

Another object of the present invention is to provide a process in which the impurities such as oily products derived from cyclopentadiene can be satisfactorily eliminated in a solution containing 2-azabicyclo[2.2.1]hept-5-en-3-one produced by the process thereby obtaining 2-azabicyclo[2.2.1] hept-5-en-3-one in a higher purity.

Since 2-azabicyclo[2.2.1]hept-5-en-3-one obtained by the conventional processes is often in the form of oil or a solid of large lumps, it is difficult to handle, e.g., when filling into a container, weighing and use for chemical synthesis, and crystals of finely divided particulate 2-azabicyclo[2.2.1] hept-5-en-3-one, having less stickiness and excellent in fluidity and handling have not yet been realized. Accordingly, another object of the present invention is to provide a process in which finely divided particulate crystals of 2-azabicyclo[2.2.1]hept-5-en-3-one can be deposited satisfactorily and in a high recovery rate.

Accordingly, the first embodiment of the present invention relates to a process for producing 2-azabicyclo[2.2.1] hept-5-en-3-one, which includes reacting sulfonyl cyanide represented by the following general formula (I):

$$R-SO_2CN \qquad (I)$$

(where R represents an alkyl group or a phenyl group which may have a substituent) with cyclopentadiene in the presence of water and in a hydrocarbon solvent at a pH of 4 to 7 inclusive.

The second embodiment of the present invention relates to a process for producing 2-azabicyclo[2.2.1]hept-5-en-3-one, which includes producing 2-azabicyclo[2.2.1]hept-5-en-3-one by the process described above in the first embodiment, separating the reaction solution containing 2-azabicyclo[2.2.1]hept-5-en-3-one into an aqueous layer and an organic layer, passing the aqueous layer through an activated carbon packed column and then isolating 2-azabicyclo[2.2.1]hept-5-en-3-one from the aqueous layer.

The third embodiment of the present invention relates to a method of crystallizing 2-azabicyclo[2.2.1]hept-5-en-3-one, which includes dissolving 2-azabicyclo[2.2.1]hept-5-en-3-one in an organic solvent mainly including at least one of diisopropyl ether and methyl tertiary butyl ether to prepare a solution, and then cooling the solution to deposit crystals of 2-azabicyclo[2.2.1]hept-5-en-3-one.

DESCRIPTION OF THE PREFERRED EMBODIMENTS

A more complete appreciation of the invention and many of the attendant advantages thereof will be readily obtained as the same becomes better understood by reference to the following detailed description, which is not intended to be limiting unless otherwise specified.

At first, a process for producing 2-azabicyclo[2.2.1]hept-5-en-3-one according to the present invention will be explained.

In the sulfonyl cyanide represented by the general formula (I) in the present invention (hereinafter simply referred to as sulfonyl cyanide (I)), R represents an alkyl group or a phenyl group with or without a substituent. If R is an alkyl group, it is preferably an alkyl group of 1 to 4 carbon atoms, specifically, methyl group, ethyl group, n-propyl group, i-propyl group, n-butyl group, i-butyl group or t-butyl group. If R is phenyl group, it is preferably a nonsubstituted phenyl group or a substituted phenyl group represented by the following formula (II):

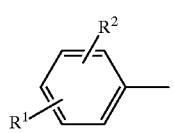

$$(II)$$

wherein $R^1$ and $R^2$ each independently represent a hydrogen atom, an alkyl group or a halogen atom.

In the formula (II), when $R^1$ and/or $R^2$ is an alkyl group, it is preferably an alkyl group of from 1 to 4 carbon atoms, and preferably, methyl group or ethyl group. Further, if $R^1$ and/or $R^2$ is a halogen atom in the formula (II), it is preferably a chlorine atom, bromine atom or fluorine atom.

Among them, the group R in the sulfonyl cyanide (I) is, more preferably methyl group, ethyl group, phenyl group or p-tolyl group and, accordingly, in the present invention, methanesulfonyl cyanide, ethanesulfonyl cyanide, benzenesulfonyl cyanide, p-toluenesulfonyl cyanide or a mixture of two or more of them is used preferably as the sulfonyl cyanide (I), and benzenesulfonyl cyanide, p-toluenesulfonyl cyanide or a mixture thereof is used more preferably.

The process for producing the sulfonyl cyanide (I) to be used in the present invention is not particularly limited, and it may be produced by any method known in the art. In addition, the purity of the sulfonyl cyanide (I) to be used in the present invention also is not particularly limited, but those having a purity of 70% or higher, and more preferably 85% or higher, are generally used preferably since aimed 2-azabicyclo[2.2.1]hept-5-en-3-one can be obtained smoothly.

The process for producing cyclopentadiene to be used in the present invention also is not particularly limited, and it may be produced by any method known in the art. In addition, there is no particular restriction on the purity of cyclopentadiene. Among them, use of cyclopentadiene formed by thermally decomposing dicyclopentadiene just after the preparation is preferred since the content of impurities is small, and post-treatment after production of 2-azabicyclo[2.2.1]hept-5-en-3-one is easy.

In the present invention, it is necessary to produce 2-azabicyclo[2.2.1]hept-5-en-3-one by reacting sulfonyl cyanide (I) and cyclopentadiene in the presence of water in a hydrocarbon solvent at a pH of 4 to 7 inclusive.

In the reaction described above, it is preferred to use cyclopentadiene at a ratio of one mol or more based on one mol of sulfonyl cyanide (I) and it is more preferred to use cyclopentadiene at a ratio of from 1 to 5 mol inclusive based on one mol of sulfonyl cyanide (I), particularly, in view of economy and ease of the post-treatment.

As the hydrocarbon solvent, any of saturated aliphatic hydrocarbon solvents, aromatic hydrocarbon solvents and mixed solvents thereof can be used. As the saturated aliphatic hydrocarbon solvent, any of saturated aliphatic hydrocarbon solvents which are liquid at the reaction temperature and inert to the reaction can be used. Linear or cyclic saturated aliphatic hydrocarbon solvents having from 4 to 10 carbon atoms can preferably be used, and specifically, pentane, hexane, heptane, octane, nonane, decane and cyclohexane can be mentioned. In addition, as the aromatic hydrocarbon solvent, any of aromatic hydrocarbon solvents which are liquid at the reaction temperature and inert to the reaction can be used, benzene, toluene and xylene being used preferably. In the present invention, the hydrocarbon solvents can be used alone or as a mixture of two or more of them.

In the reaction, the ratio of the hydrocarbon solvent to be used is preferably from 0.1 to 20 parts by weight inclusive and, more preferably, from 0.1 to 5 parts by weight inclusive based on one part by weight of sulfonyl cyanide (I). In particular, according to the present invention, even if the hydrocarbon solvent is used in an amount as small as one part by weight or less, especially, 0.5 part by weight or less based on one part by weight of sulfonyl cyanide (I), the 2-azabicyclo[2.2.1]hept-5-en-3-one can be produced smoothly without deposition of solid products such as a dimerization product (for example, benzenesulfinyl sulfone) of sulfinic acid (for example, benzenesulfinic acid), so that the process is excellent in view of economy and mitigation of the burden for treating waste water.

In the reaction, the ratio of water to be used is preferably from 0.1 to 20 parts by weight inclusive based on one part by weight of the sulfonyl cyanide (I), and it is more preferred to use water at a ratio of from 0.1 to 5 parts by weight inclusive based on one part by weight of sulfonyl cyanide (I) in view of the extraction efficiency of the 2-azabicyclo [2.2.1]hept-5-en-3-one.

The ratio of the hydrocarbon solvent and water to be used is preferably, hydrocarbon solvent:water=1:0.005~200 parts by weight inclusive and, more preferably, 1:0.2~50 parts by weight inclusive. It is preferred that the total weight of the hydrocarbon solvent and water is from 0.2 to 10 parts by weight inclusive, more preferably, from 0.2 to 5 parts by weight inclusive, based on one part by weight of sulfonyl cyanide (I) in view of the economy and the mitigation of the burden on the disposal waste water. According to the process of the present invention, the 2-azabicyclo[2.2.1]hept-5-en-3-one can be produced smoothly without deposition of solid products such as dimerization products (for example, benzenesulfinyl sulfone) of sulfinic acid (for example, benzenesulfinic acid), irrespective of the use of the hydrocarbon solvent and water in an amount as small as from 0.2 to 5 parts by weight inclusive, particularly, from 0.2 to 2.5 parts by weight inclusive.

The method of mixing sulfonyl cyanide (I) and cyclopentadiene upon conducting reaction is not particularly limited, and for example, cyclopentadiene may be added to sulfonyl cyanide (I), or sulfonyl cyanide (I) may be added to cyclopentadiene, or sulfonyl cyanide (I) and cyclopentadiene may be mixed simultaneously. In this case, the hydrocarbon solvent and water may be mixed only to one of the sulfonyl cyanide (I) and cyclopentadiene, or may be mixed to both of them, or one of the hydrocarbon solvent and water may first be mixed with the sulfonyl cyanide (I), while the remainder of the hydrocarbon solvent and water may first be mixed with cyclopentadiene. Among them, it is preferred to adopt a method of first dissolving cyclopentadiene in a mixed solvent of the hydrocarbon solvent and water, gradually adding sulfonyl cyanide (I) dropwise thereto, or first dissolving the sulfonyl cyanide (I) in a mixed solvent of the hydrocarbon solvent and water and gradually adding cyclopentadiene dropwise thereto, by which the reaction can be proceeded smoothly under moderate conditions and 2-azabicyclo[2.2.1]hept-5-en-3-one can be produced in a high yield.

It is preferred to react sulfonyl cyanide (I) and cyclopentadiene while keeping the temperature of the reaction mixture within a range of from 0 to 50° C. inclusive for preventing hydrolysis of intermediate products produced in the course of the reaction, and of 2-azabicyclo[2.2.1]hept-5-en-3-one finally produced therefrom, and it is more preferred to conduct the reaction while keeping the temperature within a range of from 5 to 30° C. inclusive.

In the present invention, it is important that the reaction of the sulfonyl cyanide (I) and cyclopentadiene is conducted while keeping the pH of the reaction mixture within a range of from 4 to 7 inclusive.

If the pH of the reaction mixture is less than 4, solid products such as dimerization products (for example, benzenesulfinyl sulfone) of sulfinic acid (for example, benzenesulfinic acid) are deposited in the reaction mixture and make stirring difficult upon reaction, and a filtration step for separating the solid products is required which makes the reaction step complicated and lowers the yield and purity of 2-azabicyclo[2.2.1]hept-5-en-3-one.

On the other hand, if the pH of the reaction mixture exceeds 7, hydrolysis of the resultant 2-azabicyclo[2.2.1] hept-5-en-3-one proceeds to lower the yield.

In the present invention, it is preferred to keep the pH of the reaction mixture within a range of from 4 to 6.5 inclusive, more preferably, from pH of 4.2 to 5.5 inclusive for preventing deposition of the solid materials, and preventing hydrolysis of 2-azabicyclo[2.2.1]hept-5-en-3-one.

As a method of keeping the pH of the reaction mixture within a range of from 4 to 7 inclusive, there is preferably adopted a method of optionally adding one or more of organic and inorganic alkali compounds, without hindering the reaction, to the reaction mixture while always observing the pH of the reaction mixture. In particular, it is preferred to keep the pH within a range of from 4 to 7 inclusive by adding an aqueous solution of one or more of inorganic alkali compounds such as alkali metal hydroxides (for example, sodium hydroxide and potassium hydroxide), alkaline earth metal hydroxides (for example, calcium hydroxide, magnesium hydroxide and barium hydroxide), alkali metal carbonates (for example, sodium carbonate and potassium carbonate), alkaline earth metal carbonates (for example, calcium carbonate, magnesium carbonate and barium carbonate), alkali metal bicarbonates (for example, sodium hydrogen carbonate and potassium hydrogen carbonate) since pH can be controlled easily.

The reaction described above is preferably conducted under stirring, so that the reaction can proceed smoothly. Preferably, the reaction time can be controlled depending on the kinds of the sulfonyl cyanide (I), the amount and the ratio of the sulfonyl cyanide (I) and cyclopentadiene to be used, the amount of the hydrocarbon solvent and water to be used, the reaction temperature, the scale of the reactor and the like, and it is generally preferred to conduct reaction for a time within a range from 30 minutes to 48 hours, more preferably 1 hour to 36 hours, including the addition time (dropping time) of the reaction ingredients.

When the reaction of the present invention is conducted by using, for example, sodium hydroxide as a pH controller of the reaction mixture, it is believed that the 2-azabicyclo [2.2.1]hept-5-en-3-one is formed according to the following reaction formula:

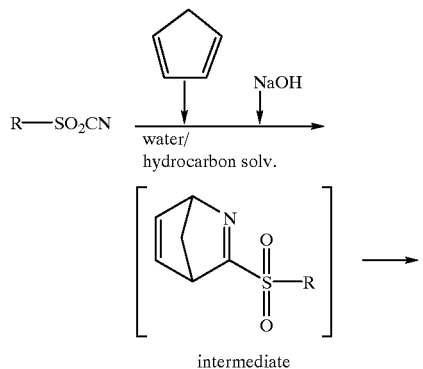

intermediate

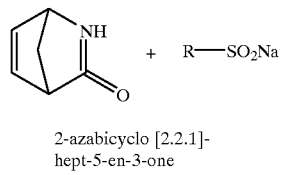

2-azabicyclo [2.2.1]-
hept-5-en-3-one (where R represents the same radical as defined above).

If the pH of the reaction mixture is out of the range of the present invention in the reaction of sulfonyl cyanide (I) and cyclopentadiene, undesired side reactions such as hydrolysis of the intermediate product for 2-azabicyclo[2.2.1]hept-5-en-3-one shown in the abovementioned reaction scheme, or hydrolysis of the 2-azabicyclo[2.2.1]hept-5-en-3-one occurs, tending to produce aminocarboxylic acid represented by the following chemical formula:

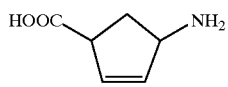

or to produce solid dimerization product (R—SO—SO$_2$—R) of sulfinic acid (R—SO$_2$H) formed by the reaction of sulfonyl cyanide (I) and cyclopentadiene.

Preferably, after reacting the sulfonyl cyanide (I) and cyclopentadiene while keeping the pH of the reaction mixture within a range of from 4 to 7 inclusive to produce the 2-azabicyclo[2.2.1]hept-5-en-3-one, the reaction can be terminated by raising the pH of the reaction mixture to greater than 7, more preferably more than 7.5, and preferably 8 or lower.

The reaction solution containing 2-azabicyclo[2.2.1]hept-5-en-3-one obtained as described above can be used without isolating 2-azabicyclo[2.2.1]hept-5-en-3-one from the reaction solution, as a starting material for synthesizing carbocyclic nucleosides, etc., but it is preferred to isolate 2-azabicyclo[2.2.1]hept-5-en-3-one from the reaction solution.

The method for isolating 2-azabicyclo[2.2.1]hept-5-en-3-one from the reaction solution is not particularly limited, and any method can be used so long as it is a method capable of isolating 2-azabicyclo[2.2.1]hept-5-en-3-one smoothly. A preferred example of the method of isolating 2-azabicyclo [2.2.1]hept-5-en-3-one from the reaction solution includes a method of separating the reaction solution containing 2-azabicyclo[2.2.1]hept-5-en-3-one into an aqueous layer and a hydrocarbon solvent layer, recovering the aqueous layer, extracting 2-azabicyclo[2.2.1]hept-5-en-3-one contained in the aqueous layer by an appropriate extraction solvent, and then distilling off the extraction solvent to give the aimed 2-azabicyclo[2.2.1]hept-5-en-3-one, by which the 2-azabicyclo[2.2.1]hept-5-en-3-one can be obtained in a high yield and a high purity. As the extraction solvent in this case, any solvent can be used so long as it is a solvent capable of extracting 2-azabicyclo[2.2.1]hept-5-en-3-one from the aqueous layer, but a chlorinated hydrocarbon solvent such as methylene chloride, chloroform or dichloroethane is preferably used.

In the isolating method as described above, if the extraction treatment by the extraction solvent is conducted after passing the aqueous layer containing 2-azabicyclo[2.2.1] hept-5-en-3-one through an activated carbon packed column or charging activated carbon in the aqueous layer to remove impurities such as oily products derived from cyclopentadiene contained in the aqueous layer, before extraction treatment of the aqueous layer by the extraction solvent, 2-azabicyclo[2.2.1]hept-5-en-3-one in a higher purity can be obtained. Among them, the method of passing the aqueous layer containing 2-azabicyclo[2.2.1]hept-5-en-3-one through the activated carbon packed column is most preferred for removing impurities. The kind of the activated carbon to be used for the removal of the impurities is not particularly limited, but any activated carbon can be used and, among them, KURARAY COAL GC-F (manufactured by Kuraray Chemical Co., Ltd.) is preferably used. The shape, the structure and the size of the activated carbon packed column are not particularly limited, and can be determined depending on situations.

2-Azabicyclo[2.2.1]hept-5-en-3-one obtained as described above, has a sufficiently high purity as such, and can be used effectively as a material for synthesizing the carbocyclic nucleoside, but it can be further purified or made easily handleable by optionally conducting distillation, activated carbon-treatment, sublimation or recrystallization further.

In the isolating step described above, sulfinate, $RSO_2M$ (M represents a salt-forming cation) remains in the aqueous layer after isolating 2-azabicyclo[2.2.1]hept-5-en-3-one by conducting extraction treatment, for example, by using the chlorinated hydrocarbon solvent. If cyanogen chloride is added to the aqueous layer containing the sulfinate after the extraction treatment, sulfinate is converted easily to sulfonyl cyanide (I), and the sulfonyl cyanide (I) produced by the conversion may be re-used as a starting material for producing 2-azabicyclo[2.2.1]hept-5-en-3-one.

According to the process of the present invention, since deposition of solid materials such as dimerization products (for example, benzenesulfinyl sulfone) of sulfinic acid (for example, benzenesulfinic acid) in the reaction mixture, troubles such as impossibility of stirring are completely avoided during the reaction, a filtration step for separating solid matter from the solution after completion of the reaction is not necessary, and the 2-azabicyclo[2.2.1]hept-5-en-3-one can be produced in a high purity and a high yield, with good industrial productivity. In addition, it is possible to conduct the reaction while reducing the amount of water and the hydrocarbon solvent to be used to remarkably mitigate the burden on treating waste water.

Since the process of the present invention includes only one step, complicated procedures of taking out the intermediate products under concentration, pulverizing them to a powder and then conducting the subsequent step are not necessary and, in addition, control of the reaction is easy and safely provided since an abrupt exothermic reaction does not occur.

In addition, in the process of the present invention, since it is not necessary to use cyclopentadiene in great excess to sulfonyl cyanide, it is excellent in economical advantage.

Further, in the present invention, when a step of passing the solution containing 2-azabicyclo[2.2.1]hept-5-en-3-one produced by the process of the present invention through the activated carbon packed column is further conducted, impurities such as oily products derived from cyclopentadiene can be removed effectively, to obtain 2-azabicyclo[2.2.1]hept-5-en-3-one in a higher purity.

A method of crystallizing 2-azabicyclo[2.2.1]hept-5-en-3-one in the present invention will be explained next.

In the method of crystallizing 2-azabicyclo[2.2.1]hept-5-en-3-one of the present invention, the preparation method, the purity and the form of the phase of 2-azabicyclo[2.2.1]hept-5-en-3-one to be used for the crystallization are not particularly limited, and it can be applied to any 2-azabicyclo[2.2.1]hept-5-en-3-one, which is used necessarily or optionally in the form of finely particulate crystals.

The 2-azabicyclo[2.2.1]hept-5-en-3-one usable in the crystallization method of the present invention is not limited but can include those obtained by the existent methods, for example, by J. C. Jagt, et al ; those obtained by the production processes (i) to (iv) by the present inventors described previously; and those obtained by the production process according to the present invention.

2-Azabicyclo[2.2.1]hept-5-en-3-one to be used in the crystallization method of the present invention may be in any form such as oil, lump, coarse powder or solution. Further, 2-azabicyclo[2.2.1]hept-5-en-3-one to be used in the crystallization method of the present invention may be one as obtained finally by the synthesizing method as exemplified above or by other synthesizing methods, or may be one as obtained in the intermediate step (for example, those before drying, in a state dissolved in an extraction solvent or dissolved in an extraction solvent and concentrated to some extent). Accordingly, the crystallization method of the present invention can be conducted independently of 2-azabicyclo[2.2.1]hept-5-en-3-one already produced separately, or it may be conducted as a part of the production step in the final step of synthesizing 2-azabicyclo[2.2.1]hept-5-en-3-one.

In the present invention, 2-azabicyclo[2.2.1]hept-5-en-3-one is dissolved in an organic solvent mainly including at least one of diisopropyl ether and methyl tertiary butyl ether to prepare a solution.

The organic solvent to be used in the present invention is preferably an organic solvent containing at least one of diisopropyl ether and methyl tertiary butyl ether at a ratio of 50% by weight or more. Among them, a preferred solvent is 100% diisopropyl ether, a mixed solvent comprising 50% by weight or more of diisopropyl ether and 50% by weight or less of other organic solvent, 100% methyl tertiary butyl ether, a mixed soivent comprising methyl tertiary butyl ether and hexane at an optional ratio or a mixed solvent comprising 50% by weight or more of methyl tertiary butyl ether and 50% by weight or less of other organic solvent. Other preferable ratios include 60/40, 70/30, and 80/20.

In particular, in the present invention, the organic solvent used preferably is 100% diisopropyl ether, a mixed solvent comprising 50% by weight or more of diisopropyl ether and 50% by weight or less of methylene chloride and/or isopropanol, especially, a mixed solvent comprising 80% by weight or more of diisopropyl ether and 20% by weight or less of methylene chloride and/or isopropanol, 100% methyl tertiary butyl ether, a mixed solvent comprising 50% by weight or more of methyl tertiary butyl ether and 50% by weight or less of hexane and, particularly, a mixed solvent comprising 60% by weight or more of methyl tertiary butyl ether and 40% by weight or less of hexane.

The concentration of 2-azabicyclo[2.2.1]hept-5-en-3-one in the solution to be used for crystallization is preferably from 5 to 30% by weight inclusive and, more preferably, from 10 to 23% by weight inclusive. If the concentration of 2-azabicyclo[2.2.1]hept-5-en-3-one in the solution exceeds 30% by weight, finely particulate crystals of 2-azabicyclo[2.2.1]hept-5-en-3-one are reduced, and they tend to be deposited in an oily form. If the oily products are further cooled continuously, they often form into solid lumps. On the other hand, if the concentration of 2-azabicyclo[2.2.1]hept-5-en-3-one in the solution is less than 5% by weight, it takes an extremely long period of time for the deposition of crystals of 2-azabicyclo[2.2.1]hept-5-en-3-one from the solution, or the crystals of 2-azabicyclo[2.2.1]hept-5-en-3-one tend to deposit no more.

Upon preparation of the solution to be used for the crystallization, the temperature for dissolving 2-azabicyclo[2.2.1]hept-5-en-3-one in the organic solvent is not particularly limited, but any temperature may be adopted at which thermal decomposition or denaturation of 2-azabicyclo-[2.2.1]hept-5-en-3-one is avoided, and can be selected depending on the kind of the organic solvent. It is generally preferred to dissolve 2-azabicyclo[2.2.1]hept-5-en-3-one in the organic solvent at a temperature within a range from 40 to 60° C. inclusive, and more preferably 45–55° C. inclusive.

Then, the solution of 2-azabicyclo[2.2.1]hept-5-en-3-one prepared as described above is cooled to deposit 2-azabicyclo[2.2.1]hept-5-en-3-one as finely divided particulate crystals.

The cooling temperature may be selected depending on the kind of organic solvent and the concentration of 2-azabicyclo[2.2.1]hept-5-en-3-one in the solution, but it is generally preferred to conduct cooling such that a final temperature is from 0 to 15° C. inclusive since the deposition of crystals is made satisfactory. The cooling rate in this case is not particularly limited, but the cooling rate of 2° C./min or lower, and preferably 1° C./min or lower, is generally preferred since finely divided particulate crystals can be deposited at a high recovery rate.

Depositing 2-azabicyclo[2.2.1]hept-5-en-3-one crystals as described above may be conducted without stirring, but it is preferred to deposit them under moderate stirring, and finely divided particulate crystals with no coagulation can be deposited more smoothly by the stirring.

In addition, seed crystals may optionally be added to the solution of 2-azabicyclo[2.2.1]hept-5-en-3-one.

In particular, when 2-azabicyclo[2.2.1]hept-5-en-3-one isolated by the production process of the present invention is dissolved in diisopropyl ether or dissolved in a mixed solvent comprising diisopropyl ether and other solvent, for example, methylene chloride to prepare a solution, and 2-azabicyclo[2.2.1]hept-5-en-3-one is crystallized from the solution, finely divided particulate crystals of 2-azabicyclo[2.2.1]hept-5-en-3-one in a high purity with excellent handleability can be obtained. In addition, instead of recrystallizing 2-azabicyclo[2.2.1]hept-5-en-3-one isolated from the extraction solvent, diisopropyl ether may be added in the extraction solution containing 2-azabicyclo[2.2.1]hept-5-en-3-one obtained by extraction treatment of the aqueous layer by using a chlorinated hydrocarbon solvent such as methylene chloride, and 2-azabicyclo[2.2.1]hept-5-en-3-one may be crystallized from the solution, in which finely particulate crystals of 2-azabicyclo[2.2.1]hept-5-en-3-one in a high purity with excellent handleability can also be obtained smoothly.

The deposited crystals of 2-azabicyclo[2.2.1]hept-5-en-3-one are preferably separated by filtration or other separation means, and optionally dried.

In the process of the present invention, finely divided particulate crystals of 2-azabicyclo[2.2.1]hept-5-en-3-one having uniform grain size, with less stickiness and excellent in fluidity and handleability can be conveniently obtained in a high recovery rate.

Since the crystals of 2-azabicyclo[2.2.1]hept-5-en-3-one obtained by such procedures exhibit finely divided particulate form, are less sticky and excellent in fluidity and handleability, they can easily be filled into a container or weighed and, further, they are especially suitable for chemical synthesis of carbocyclic nucleosides and other compounds, and separation of racemic 2-azabicyclo[2.2.1]hept-5-en-3-one into a D isomer and a L isomer.

EXAMPLES

Having generally described this invention, a further understanding can be obtained by reference to certain specific examples which are provided herein for purposes of illustration only and are not intended to be limiting unless otherwise specified.

Reference Example 1
Synthesis of benzenesulfonyl cyanide (1) In a four-necked flask (200 ml volume), 70 g of water, 2 g of methylene chloride and 32.0 g (0.16 mol) of sodium benzenesulfinate dihydrate were charged, and then cooled to 3° C. Then, 10.7 g (0.17 mol) of gaseous cyanogen chloride was introduced for about 15 min while keeping the internal temperature at 3 to 6° C. inclusive. After introducing cyanogen chloride, the reaction mixture was stirred at 5° C. for 30 min to conduct reaction and then the mixture was transferred into a separation funnel to separate into an aqueous layer and an organic layer (methylene chloride layer).

(2) To the aqueous solution separated as described above, 5 g of methylene chloride was added to apply extraction treatment, and the extract and the organic layer (methylene chloride layer) separated in (1) above were combined, dried over magnesium sulfate and then methylene chloride was distilled off under reduced pressure to obtain 24.8 g (0.14 mol, 94.3% purity) of benzenesulfonyl cyanide. The yield was 87.5%.

Reference Example 2
Synthesis of p-toluenesulfonyl cyanide

The same procedures as those in Reference Example 1 were conducted except for using 34.3 g (0.16 mol) of sodium p-toluenesulfinate instead of sodium benzenesulfinate to obtain 27.5 g (0.15 mol, purity: about 100%) of p-toluenesulfonyl cyanide. The yield was 93.8%.

Reference Example 3
Production of cyclopentadiene

Into a four-necked flask equipped with a simple distillation device (500 ml volume), 300 g (2.27 mol) of dicyclopentadiene was charged. Dicyclopentadiene was thermally decomposed and distilled while keeping the internal temperature at 155 to 160° C. inclusive and the distilling temperature at 50 to 55° C. inclusive to obtain 185 g (2.80 mol) of cyclopentadiene. The yield was 61.7%.

Example 1

(1) In a four-necked flask (500 ml volume) equipped with a nitrogen flowing tube and a thermometer, 52.9 g (0.85 mol) of cyclopentadiene obtained in Reference Example 3, 10 g of toluene and 130 g of water were charged, and the inner temperature was controlled to 10° C. Then, 103.2 g (0.58 mol, 94.3% purity) of benzenesulfonyl cyanide produced in Reference Example 1 was added dropwise from a dropping funnel while keeping the internal temperature of the four-necked flask at 8 to 15° C. inclusive for about 3 hours. During addition of benzenesulfonyl cyanide, pH of the reaction mixture in the flask was continuously measured simultaneously and an aqueous solution of 25% sodium hydroxide was added dropwise to keep the pH of the reaction mixture within a range from 4.4 to 4.7 inclusive. Reaction was further conducted for 30 min with stirring while keeping the internal temperature at 8 to 15° C. inclusive under the identical pH. In the course of the reaction, deposition of solid products in the reaction mixture were not found at all and satisfactory liquid form was maintained.

(2) Then, after adding the aqueous solution of 25% sodium hydroxide to increase the pH of the reaction mixture to 7.5, the reaction solution in the flask was transferred into a separation funnel to separate the aqueous layer.

(3) A portion of the aqueous layer as described above was sampled and subjected to the internal standard analysis by HPLC (high performance liquid chromatography) under the condition shown in the following Table 1. The amount of 2-azabicyclo[2.2.1]hept-5-en-3-one contained in the aqueous layer separated in (2) above was measured to be 52.4 g (0.48 mol, 82.8% yield).

TABLE 1

Analysis condition of HPLC

| Column: | manufactured by GL Science Co., Ltd. Inertsil ODS-2 (inner diameter: 4.6 mm, length: 150 mm) |
| --- | --- |
| Eluent: | methanol/1 mM aqueous solution of potassium dihydrogen phosphate (adjusted to pH 3.2 with 1M phosphoric acid) = 2/8 (volume ratio) mixed solution |
| Flow rate: | 1 ml/min |
| Detection wavelength: | UV at a wavelength of 225 nm |

(4) Extracting a remaining portion of the aqueous layer separated in (2) above (remaining portion not used for HPLC) by using 40 g of methylene chloride were repeated for 5 times (the total amount of methylene chloride used: 200 g) and then methylene chloride was distilled off under reduced pressure to obtain skin-colored 2-azabicyclo[2.2.1]hept-5-en-3-one. The purity of the thus obtained 2-azabicyclo[2.2.1]hept-5-en-3-one was 95.1%.

(5) The physical properties and the result of analysis of 2-azabicyclo[2.2.1]hept-5-en-3-one obtained in (4) above were as below.

mp 55.8–56.8° C.;

$^1$H—NMR (CDCl$_3$, TMS, ppm) δ:2.22 (d), 2.39 (d, 2H, —CH$_2$—), 3.22 (s, 1H, —CH—C=O), 4.35 (s, 1H, —CH—NH—), 6.26 (s, 1H, —NH—), 6.77 (m, 1H, =CH—C—C=O), 6.81 (m, 1H, =CH—C—N);

$^3$C—NMR(CDCl$_3$, TMS, ppm) δ:53.1 (—CH$_2$—), 59.2 (CH—C=O), 60.2 (CH—NH—), 138.0 (=CH—CH—C=O), 141.1 (=CH—CH—NH), 185.3 (—C=O).

Example 2

(1) The same procedures as in (1) and (2) of Example 1 were conducted, and the reaction solution in the flask controlled to pH 7.5 was transferred to a separation funnel to separate the aqueous layer.

(2) After passing the aqueous layer obtained in (1) above through an activated carbon packed column (activated carbon: "KURARAY COAL GC-F", column =20 mm inner diameter×75 mm length, manufactured by Kuraray Chemical Co., Ltd.), extraction treatment by using methylene chloride was repeated for five times in the same manner as in (4) of Example 1, and then methylene chloride was distilled off under reduced pressure to obtain pale skin-colored 2-azabicyclo[2.2.1]hept-5-en-3-one, The purity of the thus obtained 2-azabicyclo[2.2.1]hept-5-en-3-one was 98.2%.

(3) Then, 80 g of diisopropyl ether was added to 20 g of 2-azabicyclo[2.2]hept-5-en-3-one obtained in (2) above and dissolved by being heated to 50° C., cooled gradually to 10° C. while stirring for 30 min, and further stirred at 10° for 30 min to obtain fine crystals of 2-azabicyclo[2.2.1]hept-5-en-one. When the thus obtained crystals were dried at 45° C. (100 mmHg), they were of uniform grain size, not sticky and excellent in fluidity and handleability.

Example 3

(1) In a four-necked flask (500 ml volume) equipped with a nitrogen flowing tube and a thermometer, 103.2 g (0.58 mol) of benzenesulfonyl cyanide (94.3% purity) obtained in Reference Example 1, 10 g of toluene and 130 g of water were charged and the internal temperature was controlled to 10° C. 52.9 g (0.80 mol) of cyclopentadiene obtained in Reference Example 3 was added dropwise thereto from a dropping funnel for about 3 hours while keeping the internal temperature of the four-necked flask at from 8 to 15° C., inclusive. During addition of cyclopentadiene, pH of the reaction mixture in the flask was continuously measured simultaneously, and an aqueous solution of 25% sodium hydroxide was added dropwise to keep the pH of the reaction mixture within a range of from 4.4 to 4.7 inclusive. Reaction was further conducted for 30 min with stirring while keeping the internal temperature at from 8 to 15° C. inclusive under the identical pH. In the course of the reaction, deposition of solid products in the reaction mixture was not observed at all and satisfactory liquid form was maintained.

(2) Then, after adding the aqueous solution of 25% sodium hydroxide to increase pH of the reaction mixture to 7.5, the reaction solution in the flask was transferred into a separation funnel to separate an aqueous layer.

(3) A portion of the aqueous layer as described above was sampled and subjected to the internal standard analysis by HPLC under the conditions shown in Table 1, and the amount of 2-azabicyclo[2.2.1]hept-5-en-3-one contained in the aqueous layer separated in (2) above was determined to be 51.2 g (0.47 mol, 81.0% yield).

Example 4

The same procedures as those in (1) and (2) of Example 1 were conducted except for using 110.5 g (0.58 mol) of p-toluenesulfonyl cyanide instead of benzenesulfonyl cyanide. As a result of subjecting the aqueous layer obtained by the procedures to the internal standard analysis by HPLC under the conditions shown in Table 1, 50.1 g (0.46 mol, 79.3% yield) of 2-azabicyclo[2.2.1]hept-5-en-3-one was produced.

Example 5

(1) In a four-necked flask (500 ml volume) equipped with a nitrogen flowing tube and a thermometer, 52.9 g (0.80 mol) of cyclopentadiene, 10 g of toluene and 130 g of water were charged and the internal temperature was controlled to 10° C. Then, 103.2 g (94.3% purity, 0.58 mol) of benzenesulfonyl cyanide was added dropwise from a dropping funnel for about 3 hours while keeping the internal temperature of the four necked flask at 8 to 15° C. inclusive. During addition of benzenesulfonyl cyanide, the pH of the reaction mixture in the flask was continuously measured simultaneously and an aqueous solution of 25% sodium hydroxide was added dropwise to keep the pH of the reaction mixture within a range from 4.4 to 4.7 inclusive. Reaction was further conducted for 30 min with stirring while keeping the internal temperature at 8 to 15° C. inclusive under the identical pH.

(2) Then, after adding the aqueous solution of 25% sodium hydroxide to increase the pH of the reaction mixture to 7.5, the reaction solution in the flask was transferred to a separation funnel to separate an aqueous layer.

(3) Extracting the aqueous layer separated in (2) above by using 40 g of methylene chloride were repeated for 5 times (total amount of methylene chloride used: 200 g), and then a portion of methylene chloride was distilled off under reduced pressure to obtain 50 g of a concentrated solution containing 2-azabicyclo[2.2.1]hept-5-en-3-one dissolved therein.

(4) After adding 133 g of diisopropyl ether to 50 g of the concentrated solution containing 2-azabicyclo[2.2.1]hept-5-en-3-one obtained in (3) above and dissolving the same by heating to 50° C., the solution was cooled gradually to 10° C. for 30 min with stirring, and kept at 10° C. for further 30 min with stirring, finely divided particulate crystals of 2-azabicyclo[2.2.1]hept-5-en-3-one were deposited. When the thus obtained crystals were dried at 45° C. (100 mmHg), they were of a uniform grain size, not sticky and excellent in fluidity and handleability (65% yield of 2-azabicyclo [2.2.1]hept-5-en-3-one based on the amount of benzenesulfonyl cyanide used).

Comparative Example 1

(1) Benzenesulfonyl cyanide and cyclopentadiene were reacted by the same procedures as those in (1) of Example 1 except for not adding the aqueous solution of sodium hydroxide. As a result, the pH of the reaction mixture was always 3 or lower (within a range of from 2 to 3 inclusive) after three minutes from the starting of the reaction. Solid products were gradually deposited in the course of the reaction. The reaction solution obtained by the procedure was filtered by using a glass filter. When solid products remained on the glass filter were analyzed, it was found that they were mainly comprised of benzenesulfinyl sulfone as a dimerization product of benzenesulfinic acid.

(2) Then, an aqueous solution of 25% sodium hydroxide was added to the filtrate obtained in (1) described above to increase the pH to 7.5, and transferred to a separation funnel to separate an aqueous layer.

(3) When a portion of the aqueous layer as described above was sampled and subjected to the internal standard analysis in HPLC under the condition shown in Table 1 above, the amount of 2-azabicyclo[2.2.1]hept-5-en-3-one formed and contained in the aqueous layer was determined to be 45.8 g (0.42 mol, 72% yield).

(4) Extracting the aqueous layer separated in (2) above by using 40 g of methylene chloride were repeated for 5 times (the total amount of methylene chloride used: 200 g), and then methylene chloride was distilled off under reduced pressure to obtain skin-colored 2-azabicyclo[2.2.1]hept-5-en-3-one. The purity of the thus obtained 2-azabicyclo [2.2.1]hept-5-en-3-one was 95.1%.

Comparative Example 2

(1) Same procedures as those in (1) of Example 1 were conducted except for using 10 g of acetone instead of toluene in (1) of Example 1, and adding dropwise an aqueous solution of 25% sodium hydroxide to keep the pH of the reaction mixture within a range from 3.5 to 4 inclusive. As a result, a small amount of solid products was gradually deposited in the course of the reaction. The reaction solution obtained by the procedure was filtered by using a glass filter. When solid products remained on the glass filter were analyzed, it was found that they were mainly comprised of benzenesulfinyl sulfone as a dimerization product of benzenesulfinic acid.

(2) Then, an aqueous solution of 25% sodium hydroxide was added to the filtrate obtained in (1) described above to increase the pH to 7.5, and they were transferred to a separation funnel to separate an aqueous layer.

(3) When a portion of the aqueous layer described above was sampled and subjected to the internal standard analysis in HPLC under the condition shown in Table 1 above, the amount of 2-azabicyclo[2.2.1]hept-5-en-3-one formed and contained in the aqueous layer was determined to be 44.7 g (0.41 mol, 70.7% yield).

(4) Extracting the remaining aqueous layer separated in (2) above (remaining portion not used for HPLC) by using 40 g of methylene chloride were repeated for 5 times (total amount of methylene chloride used: 200 g), and then methylene chloride was distilled off under reduced pressure to obtain skin colored 2-azabicyclo[2.2.1]hept-5-en-3-one. The purity of the thus obtained 2-azabicyclo[2.2.1]hept-5-en-3-one was 95.6%.

Reference Example 4

In a four-necked flask (500 ml volume), 276.5 g of toluene solution of p-toluenesulfonyl cyanide (concentration: 61.5% by weight, 0.940 mol) and 31.75 g of toluene were charged and 89.5 g (1.35 mol),of cyclopentadiene was added. After reacting at 20 to 30° C. inclusive for 45 min, the reaction solution was cooled to 5° C., 261.5 g of water was added, and stirred at 30° C. or lower for 30 min. The reaction solution was filtered to remove a sulfinyl sulfone compound as by-product and separated to an aqueous layer and a toluene layer by using a separation funnel. The aqueous layer was neutralized to pH 8 by using an aqueous solution of sodium hydroxide. The toluene layer was extracted with 125 g of water, the extracted aqueous layer was neutralized to pH 8 by an aqueous solution of sodium hydroxide. Both of the aqueous layers were combined, and extracted with 400 g of methylene chloride for 3 times. The liquid extract of methylene chloride was concentrated under reduced pressure to obtain 89.0 g of crude product. The crude product was distilled to obtain 67.5 g of 2-azabicyclo[2.2.1]hept-5-en-3-one (boiling point: 85~90° C./1 mmHg; melting point: 55.0~57.0° C.). 2-Azabicyclo[2.2.1]hept-5-en-3-one obtained in this example was white solid lumps.

Example 6

(1) Into a three-necked flask (100 ml volume), 5 g of 2-azabicyclo[2.2.1]hept-5-en-3-one obtained in Reference Example 4 described above was charged, to which 20 g of diisopropyl ether was added and heated to 50° C. to dissolve 2-azabicyclo[2.2.1]hept-5-en-3-one to prepare a 20 wt % diisopropyl ether solution of 2-azabicyclo[2.2.1]hept-5-en-3-one.

(2) The 20 wt % diisopropyl ether solution of 2-azabicyclo [2.2.1]hept-5-en-3-one obtained in (1) above was cooled gradually to 10° C. for 30 min with stirring (150 rpm) and further stirred at 10° C. for 30 min. As a result, finely divided particulate crystals of 2-azabicyclo[2.2.1]hept-5-en-3-one were deposited. During the process, neither deposition of oily 2-azabicyclo[2.2.1]hept-5-en-3-one nor adhesion of crystals on the wall surface of the flask was observed.

(3) When the crystals of 2-azabicyclo[2.2.1]hept-5-en-3-one obtained above were dried at 45° C. (100 mmHg), and the weight was measured, it was 4.5 g and the recovery rate was 90%. The obtained crystals of 2-azabicyclo[2.2.1]hept-5-en-3-one were of uniform grain size, not sticky and excellent in fluidity and handleability.

Example 7

(1) Diisopropyl ether solutions having concentrations of 2-azabicyclo[2.2.1]hept-5-en-3-one of 10% by weight and 30% by weight were prepared respectively by changing the amount of 2-azabicyclo[2.2.1]hept-5-en-3-one dissolved in diisopropyl ether in (1) of Example 6.

(2) Crystallization was conducted in the same manner as in (2) of Example 6 by using the solutions of 2-azabicycio [2.2.1]hept-5-en-3-one obtained in (1) described above.

As a result, with the diisopropyl ether solution at the concentration of 2-azabicyclo[2.2.1]hept-5-en-3-one of 10% by weight, finely divided particulate crystals of 2-azabicyclo[2.2.1]hept-5-en-3-one were obtained and the recovery rate was 78%.

Further, with the diisopropyl ether solution at the concentration of 2-azabicyclo[2.2.1]hept-5-en-3-one of 30% by weight, formation of oily 2-azabicyclo[2.2.1]hept-5-en-3-one and deposition of the crystals on the wall surface of the flask were slightly observed, and the recovery rate of the finely divided particulate 2-azabicyclo[2.2.1]hept-5-en-3-one was 93%.

Example 8

Crystallization of 2-azabicyclo[2.2.1]hept-5-en-3-one was conducted in the same manner as in (1) and (2) of Example 6, except for using 20 g of a mixed solvent comprising 20 parts by weight of diisopropyl ether and 1 part by weight of isopropanol, as a crystallization solvent, instead of 20 g of diisopropyl ether, and changing the final cooling, temperature upon crystallization to 3° C. As a result, finely divided particulate crystals of 2-azabicyclo[2.2.1]hept-5-en-3-one were obtained at a recovery rate of 74%. The obtained crystals of 2-azabicyclo[2.2.1]hept-5-en-3-one were of uniform grain size, not sticky and excellent in fluidity and handleability. In Example 8, neither deposition of oily 2-azabicyclo[2.2.1]hept-5-en-3-one nor adhesion of crystals on the wall surface of the flask was observed.

Example 9

Crystallization of 2-azabicyclo[2.2.1]hept-5-en-3-one was conducted in the same manner as in (1) and (2) of Example 6, except for using 15 g of methyl tertiary butyl ether, as a crystallization solvent, instead of 20 g of diisopropyl ether, and changing the final cooling temperature to 3° C., to obtain finely divided particulate crystals of 2-azabicyclo[2.2.1]hept-5-en-3-one at a recovery rate of 78%. The obtained crystals of 2-azabicyclo [2.2.1]hept-5-en-3-one were of uniform grain size, not sticky and extremely excellent in fluidity and handleability. In addition, in Example 9, neither deposition of oily 2-azabicyclo[2.2.1]hept-5-en-3-one nor adhesion of crystals on the wall surface of the flask was observed.

Example 10

Crystallization of 2-azabicyclo[2.2.1]hept-5-en-3-one was conducted in the same manner as in (1) and (2) of Example 6, except for using 20 g of a mixed solvent comprising 60 parts by weight of methyl tertiary butyl ether and 40 parts by weight of hexane, as a crystallization solvent, instead of 20 g of diisopropyl ether, and changing the final cooling temperature to 3° C., to obtain finely divided particulate crystals of 2-azabicyclo[2.2.1]hept-5-en-3-one at a recovery rate of 88%. The obtained crystals of2-azabicyclo[2.2.1]hept-5-en-3-one were of uniform grain size, not sticky and extremely excellent in fluidity and handleability. In addition, in Example 10, neither deposition of oily 2-azabicyclo[2.2.1]hept-5-en-3-one nor adhesion of crystals on the wall surface of the flask was observed.

Comparative Example 3

Crystallization of 2-azabicyclo[2.2.1]hept-5-en-3-one was conducted in the same manner as in (1) and (2) of Example 6, except for using 20 g of toluene, as a crystallization solvent, instead of 20 g of diisopropyl ether. Crystals were not deposited at all, and oily products were not deposited as well.

Comparative Example 4

Crystallization of 2-azabicyclo[2.2.1]hept-5-en-3-one was conducted in the same manner as in (1) and (2) of Example 6, except for using 20 g of a mixed solvent comprising 5 parts by weight of hexane and 1 part by weight of ethyl acetate as a crystallization solvent instead of 20 g of diisopropyl ether, and changing the final cooling temperature upon crystallization to 4° C. Crystals were not deposited at all, and oily 2-azabicyclo[2.2.1]hept-5-en-3-one was deposited.

Comparative Examples 5 and 6

Crystallization of 2-azabicyclo[2.2.1]hept-5-en-3-one was conducted in the same manner as in (1) and (2) of Example 6 except for using 20 g of a mixed solvent comprising 2 parts by weight of hexane and 1 part by weight of toluene (Comparative Example 5) or 20 g of a mixed solvent comprising 2 parts by weight of hexane and 1 part by weight of acetone (Comparative Example 6), as a crystallization solvent, instead of 20 g of diisopropyl ether, and changing the final cooling temperature upon crystallization to 4° C. In both of Comparative Examples 5 and 6, crystals were not deposited at all, and the solution was separated into two layers, in which an oil layer comprising 2-azabicyclo[2.2.1]hept-5-en-3-one settled as a lower layer.

This application is based on Japanese Application Nos. 09 366169 and 09 366170, both filed Dec. 25, 1997, the entire contents of each of which are hereby incorporated by reference.

Having now fully described the invention, it will be apparent to one of ordinary skill in the art that many changes and modifications can be made thereto without departing from the spirit or scope of the invention as set forth herein.

What is claimed is:

1. A process for producing 2-azabicyclo[2.2.1]hept-5-en-3-one, comprising:

reacting a sulfonyl cyanide represented by the following formula (I):

$$R-SO_2CN \qquad (I)$$

wherein R represents an optionally substituted alkyl group or optionally substituted phenyl group, with cyclopentadiene in the presence of water and in a hydrocarbon solvent at a pH of 4 to 7 inclusive.

2. The process of claim 1, wherein R is an alkyl group selected from the group consisting of methyl group, ethyl group, n-propyl group, i-propyl group, n-butyl group, i-butyl group and t-butyl group.

3. The process of claim 1, wherein R is phenyl group selected from the group consisting of a nonsubstituted phenyl group and a substituted phenyl group represented by the following formula (II):

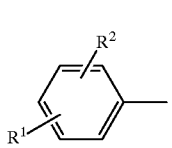

(II)

wherein $R^1$ and $R^2$ each independently represent a hydrogen atom, an alkyl group or a halogen atom.

4. The process of claim 1, wherein the cyclopentadiene is present at a ratio of one mol or more based on one mol of sulfonyl cyanide (I).

5. The process of claim 1, wherein the hydrocarbon solvent is selected from the group consisting of saturated aliphatic hydrocarbon solvent, aromatic hydrocarbon solvent and mixed solvents thereof.

6. The process of claim 1, wherein the hydrocarbon solvent is present in an amount of from 0.1 to 20 parts by weight inclusive based on one part by weight of sulfonyl cyanide (I).

7. The process of claim 1, wherein the water is present in an amount of from 0.1 to 20 parts by weight inclusive based on one part by weight of sulfonyl cyanide (I).

8. The process of claim 1, wherein the ratio of the hydrocarbon solvent and water, hydrocarbon solvent: water, is 1:0.005~200 parts by weight inclusive.

9. The process of claim 1, wherein the temperature of the reaction ranges from 0 to 50° C. inclusive.

10. The process of claim 1, wherein the pH ranges from 4 to 6.5 inclusive.

11. A process for producing 2-azabicyclo[2.2.1]hept-5-en-3-one, comprising:

reacting a sulfonyl cyanide represented by the following formula (I):

R—SO₂CN    (I)

wherein R represents an optionally substituted alkyl group or optionally substituted phenyl group, with cyclopentadiene in the presence of water and in a hydrocarbon solvent at a pH of 4 to 7 inclusive, to form a reaction solution containing 2-azabicyclo[2.2.1]hept-5-en-3-one, separating the reaction solution into an aqueous layer and an organic layer, passing the aqueous layer through an activated carbon packed column, and isolating 2-azabicyclo[2.2.1]hept-5-en-3-one from the aqueous layer.

12. The process of claim 11, wherein R is an alkyl group selected from the group consisting of methyl group, ethyl group, n-propyl group, i-propyl group, n-butyl group, i-butyl group and t-butyl group.

13. The process of claim 11, wherein R is phenyl group selected from the group consisting of nonsubstituted phenyl group and a substituted phenyl group represented by the following formula (II):

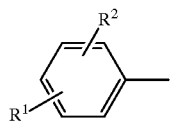

(II)

wherein $R^1$ and $R^2$ each independently represent a hydrogen atom, an alkyl group or a halogen atom.

* * * * *